US010746682B2

(12) United States Patent
Young (10) Patent No.: US 10,746,682 B2
(45) Date of Patent: Aug. 18, 2020

(54) WIRELESS SENSOR WITH MULTIPLE SENSING OPTIONS

(71) Applicant: RFMicron, Inc., Austin, TX (US)

(72) Inventor: Brian David Young, Austin, TX (US)

(73) Assignee: RFMicron, Inc., Austin, TX (US)

( * ) Notice: Subject to any disclaimer, the term of this patent is extended or adjusted under 35 U.S.C. 154(b) by 465 days.

(21) Appl. No.: 15/431,042

(22) Filed: Feb. 13, 2017

(65) Prior Publication Data

US 2017/0160220 A1    Jun. 8, 2017

Related U.S. Application Data

(63) Continuation-in-part of application No. 14/879,088, filed on Oct. 8, 2015, now Pat. No. 9,582,981.

(Continued)

(51) Int. Cl.
*G01N 27/04* (2006.01)
*G06K 19/07* (2006.01)
(Continued)

(52) U.S. Cl.
CPC .......... *G01N 27/048* (2013.01); *A61F 13/42* (2013.01); *G01N 27/045* (2013.01); *G06K 19/0717* (2013.01); *G08B 21/20* (2013.01); *G08C 17/00* (2013.01); *H04Q 9/00* (2013.01); *A61F 2013/424* (2013.01); *G01N 27/225* (2013.01);
(Continued)

(58) Field of Classification Search
CPC ............... G01N 27/048; G01N 27/045; G01N 2035/00881; G01N 27/225; H04Q 9/00; H04Q 2209/40; H04Q 2209/80; H04Q 2209/47; G08C 17/00; A61F 13/42; A61F 2013/424; G06K 19/0717; G06K 19/0723; G06K 7/10366; G06K 19/0716; G06K 19/07749; G06K 7/10148; G06K 7/10316; G06K 7/10346; G08B 21/20; H04W 88/02; H01Q 1/2225; H01Q 1/38; H01Q 5/335

See application file for complete search history.

(56) References Cited

U.S. PATENT DOCUMENTS 4,771,846 A * 9/1988 Venable ................. B62D 5/005
180/422
6,639,517 B1 * 10/2003 Chapman ................ G01M 3/16
137/312

(Continued)

*Primary Examiner* — Lee E Rodak
(74) *Attorney, Agent, or Firm* — Garlick & Markison; Timothy W. Markison (57) ABSTRACT

A wireless sensor includes an antenna, a sensing integrated circuit (IC), and a power supply impedance altering element. The antenna is operable to receive an inbound radio frequency (RF) signal and to transmit an outbound RF signal. The sensing IC includes a power supply, a first power supply connection, and a second power supply connection. The power supply impedance altering element is coupled to the first and second power supply connections and is coupled to sense a condition of an item. The sensing IC is operable to detect an impedance change of the power supply based on an effect of the power supply impedance altering element. The sensing IC is further operable to convert the impedance change into a digital value that represents the condition of the item. The sensing IC is further operable to output, via the antenna, the digital value or a representation of the condition.

8 Claims, 7 Drawing Sheets

Related U.S. Application Data (60) Provisional application No. 62/295,024, filed on Feb. 13, 2016, provisional application No. 62/061,257, filed on Oct. 8, 2014, provisional application No. 62/079,369, filed on Nov. 13, 2014, provisional application No. 62/147,890, filed on Apr. 15, 2015, provisional application No. 62/195,038, filed on Jul. 21, 2015.

(51) Int. Cl.
| | |
|---|---|
| *G08C 17/00* | (2006.01) |
| *H04Q 9/00* | (2006.01) |
| *G08B 21/20* | (2006.01) |
| *A61F 13/42* | (2006.01) |
| *H04W 88/02* | (2009.01) |
| *G01N 27/22* | (2006.01) |
| *G01N 35/00* | (2006.01) |

(52) U.S. Cl.
CPC ............. *G01N 2035/00881* (2013.01); *H04Q 2209/40* (2013.01); *H04Q 2209/80* (2013.01); *H04W 88/02* (2013.01)

(56) References Cited

U.S. PATENT DOCUMENTS

| | | | |
|---|---|---|---|
| 2009/0322543 A1* | 12/2009 | Crnkovich | A61F 13/42 340/604 |
| 2010/0225482 A1* | 9/2010 | Kasai | G06K 19/0717 340/572.1 |
| 2014/0091811 A1* | 4/2014 | Potyrailo | G06K 19/0717 324/602 |
| 2015/0346127 A1* | 12/2015 | Kalinichev | G01N 27/048 361/86 |
| 2017/0286820 A1* | 10/2017 | Nikunen | H04Q 9/00 |
| 2017/0337461 A1* | 11/2017 | Jesme | G01J 5/02 |

\* cited by examiner

WIRELESS SENSOR WITH MULTIPLE SENSING OPTIONS

CROSS REFERENCE TO RELATED PATENTS

The present U.S. Utility Patent Application claims priority pursuant to 35 U.S.C. § 119(e) to U.S. Provisional Application No. 62/295,024, entitled "RFID Sensing Using Power Supply Terminals", filed Feb. 13, 2016, which is hereby incorporated herein by reference in its entirety and made part of the present U.S. Utility Patent Application for all purposes.

The present U.S. Utility Patent Application further claims priority pursuant to 35 U.S.C. § 120 as a continuation-in-part of U.S. Utility application Ser. No. 14/879,088, entitled "Radio Frequency Identification (RFID) Moisture Tag(s) And Sensors With Extended Sensing Via Capillaries", filed Oct. 8, 2015, issuing as U.S. Pat. No. 9,582,981 on Feb. 28, 2017, which claims priority pursuant to 35 U.S.C. 119(e) to U.S. Provisional Application No. 62/061,257, entitled "Radio Frequency Identification (RFID) Moisture Tags and Sensors", filed Oct. 8, 2014, U.S. Provisional Application No. 62/079,369, entitled "Radio Frequency Identification (RFID) Moisture Tags and Sensors", filed Nov. 13, 2014, U.S. Provisional Application No. 62/147,890, entitled "Radio Frequency Identification (RFID) Moisture Tags and Sensors with Extended Sensing", filed Apr. 15, 2015, and U.S. Provisional Application No. 62/195,038, entitled "RFID Moisture Tags and Sensors with Extended Sensing via Capillaries", filed Jul. 21, 2015.

STATEMENT REGARDING FEDERALLY SPONSORED RESEARCH OR DEVELOPMENT

Not Applicable

INCORPORATION-BY-REFERENCE OF MATERIAL SUBMITTED ON A COMPACT DISC

Not Applicable

BACKGROUND OF THE INVENTION

Technical Field of the Invention

This invention relates generally to wireless communications and more particularly to wireless sensors and applications thereof.

Description of Related Art

Wireless communication systems are known to include wireless transceivers that communication directly and/or over a wireless communication infrastructure. In direct wireless communications, a first wireless transceiver includes baseband processing circuitry and a transmitter to convert data into a wireless signal (e.g., radio frequency (RF), infrared (IR), ultrasound, near field communication (NFC), etc.). Via the transmitter, the first wireless transceiver transmits the wireless signal. When a second wireless transceiver is in range (e.g., is close enough to the first wireless transceiver to receive the wireless signal at a sufficient power level), it receives the wireless signal via a receiver and converts the signal into meaningful information (e.g., voice, data, video, audio, text, etc.) via baseband processing circuitry. The second wireless transceiver may wirelessly communicate back to the first wireless transceiver in a similar manner.

Examples of direct wireless communication (or point-to-point communication) include walkie-talkies, Bluetooth, ZigBee, Radio Frequency Identification (RFID), etc. As a more specific example, when the direct wireless communication is in accordance with RFID, the first wireless transceiver may be an RFID reader and the second wireless transceiver may be an RFID tag.

For wireless communication via a wireless communication infrastructure, a first wireless communication device transmits a wireless signal to a base station or access point, which conveys the signal to a wide area network (WAN) and/or to a local area network (LAN). The signal traverses the WAN and/or LAN to a second base station or access point that is connected to a second wireless communication device. The second base station or access point sends the signal to the second wireless communication device. Examples of wireless communication via an infrastructure include cellular telephone, IEEE 802.11, public safety systems, etc.

In many situations, direct wireless communication is used to gather information that is then communicated to a computer. For example, an RFID reader gathers information from RFID tags via direct wireless communication. At some later point in time (or substantially concurrently), the RFID reader downloads the gathered information to a computer via a direct wireless communication or via a wireless communication infrastructure.

In many RFID systems, the RFID tag is a passive component. As such, the RFID tag has to generate one or more supply voltages from the RF signals transmitted by the RFID reader. Accordingly, a passive RFID tag includes a power supply circuit that converts the RF signal (e.g., a continuous wave AC signal) into a DC power supply voltage. The power supply circuit includes one or more diodes and one or more capacitors. The diode(s) function to rectify the AC signal and the capacitor(s) filter the rectified signal to produce the DC power supply voltage, which powers the circuitry of the RFID tag.

Once powered, the RFID tag receives a command from the RFID reader to perform a specific function. For example, if the RFID tag is attached to a particular item, the RFID tag stores a serial number, or some other identifier, for the item. In response to the command, the RFID tag retrieves the stored serial number and, using back-scattering, the RFID tag transmits the retrieved serial number to the RFID reader.

For instance, in automobiles, wireless tire pressure monitoring sensors are used to provide tire pressure information to an automobile's computer. The sensors may indirectly or directly sense tire pressure. For example, indirect sensing calculates tire pressure from measured revolutions of the tire via the sensor. As another example, direct sensing measures the tire pressure from inside the tire. Direct sensing provides a more accurate measure of tire pressure than indirect sensing, but does so at a cost. In particular, direct wireless sensors include a battery and micro-electromechanical semiconductor (MEMS) circuitry to sense the tire pressure.

DETAILED DESCRIPTION OF THE INVENTION

Figure 1:
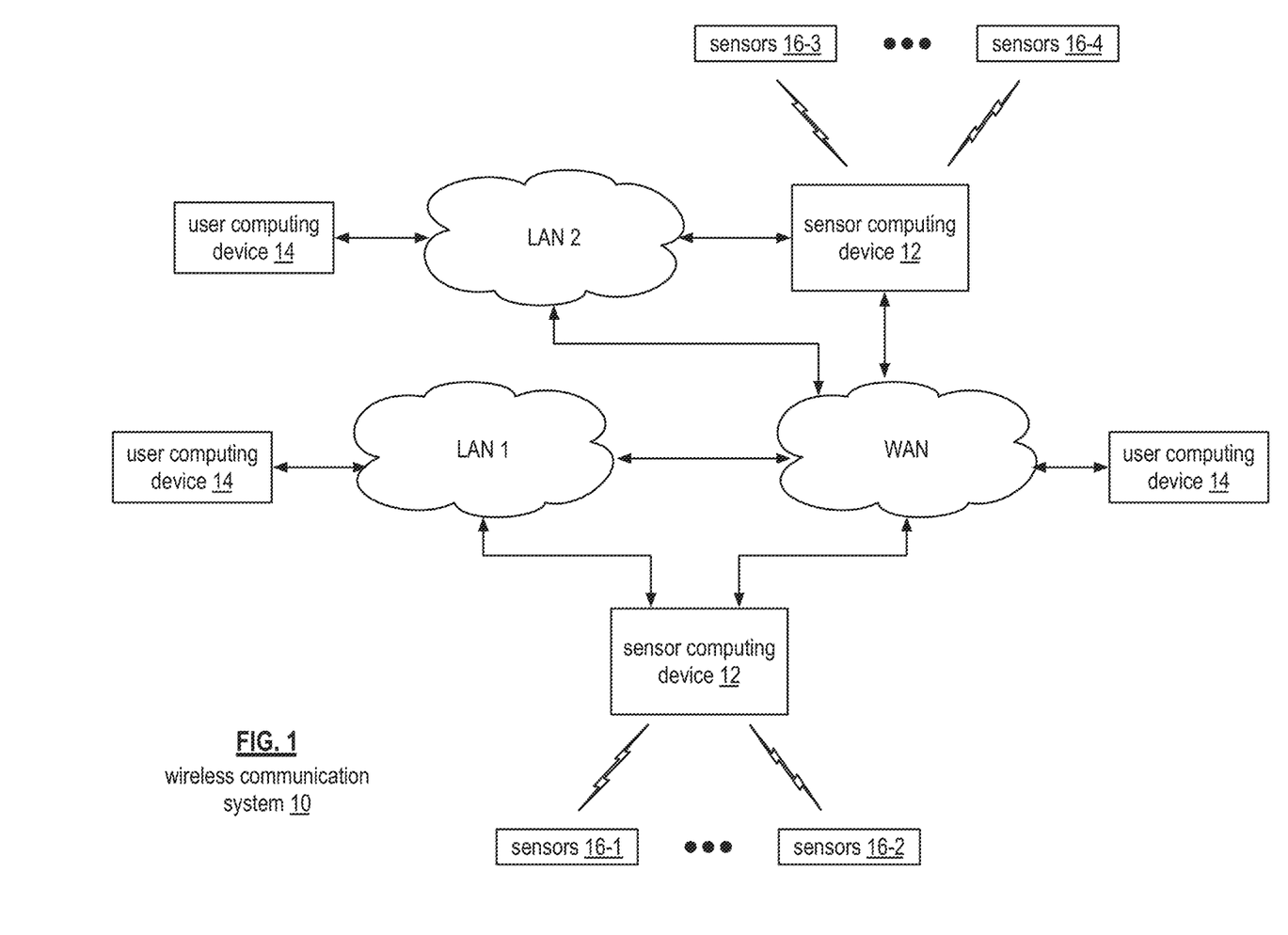
FIG. 1 is a schematic block diagram of an embodiment of a communication system in accordance with the present invention.

FIG. 1 is a schematic block diagram of an embodiment of a communication system 10 that includes a plurality of sensor computing device 12, a plurality of user computing devices 14, a plurality of wireless sensors 16-1 through 16-4 (e.g., passive or active), one or more wide area networks (WAN), and one or more local area networks (LAN). The wireless sensors 16-1 through 16-4, when activated, sense one or more of a variety of conditions. For example, one wireless sensor senses for the presence, absence, and/or amount of moisture in a given location (e.g., in a room, in a manufactured item or component thereof (e.g., a vehicle), in a bed, in a diaper, etc.). As another example, a wireless sensor senses pressure on and/or in a particular item (e.g., on a seat, on a bed, in a tire, etc.).

As yet another example, a wireless sensor senses temperature within a space and/or of an item (e.g., surface temperature of the item, in a confined space such as a room or a box, etc.). As a further example, a wireless sensor senses humidity within a space (e.g., a room, a closet, a box, a container, etc.). As a still further example, a wireless sensor senses the presence and/or percentages of a gas within a space (e.g., carbon monoxide in a car, carbon monoxide in a room, gas within a food container, etc.). As an even further example, a wireless sensor senses the presence and/or percentages of light within a space. As yet a further example, a wireless sensor senses the presence, percentages, and/or properties of one or more liquids in a solution. In one more example, a wireless sensor senses location proximity of one item to another and/or the proximity of the wireless sensor to an item (e.g., proximity to a metal object, etc.).

In general, the sensor computing devices 12 function to collect the sensed data from the wireless sensors and process the sensed data. For example, a wireless sensor generates a coded value representative of a sensed condition (e.g., amount of moisture). A sensor computing device 12 receives the coded value and processes it to determine an accurate measure of the sensed condition (e.g., a value corresponding to the amount of moisture such as 0% saturated, 50% saturated, 100% saturated, etc.).

The user computing devices 14 communicate with one or more of the sensor computing devices 12 to gather the accurate measures of sensed conditions for further processing. For example, assume that the wireless communication system is used by a manufacturing company that has multiple locations for assembly of its products. In particular, LAN 1 is at a first location where a first set of components of products are processed and the LAN 2 is at a second location where second components of the products and final assembly of the products occur. Further assume that the corporate headquarters of the company is at a third location, where it communicates with the first and second locations via the WAN and LANs.

In this example, the sensor computing device 12 coupled to LAN 1 collects and processes data regarding the first set of components as sensed by wireless sensors 16-1 and 16-2. The sensor computing device 12 is able to communicate this data to the user computing device 14 coupled to the LAN 1 and/or to the computing device 14 at corporate headquarters via the WAN. Similarly, the sensor computing device 12 coupled to LAN 2 collects and processes data regarding the second set of components and final assembly as sensed by wireless sensors 16-3 and 16-4. This sensor computing device 12 is able to communicate this data to the user computing device 14 coupled to the LAN 2 and/or to the computing device 14 at corporate headquarters via the WAN. In such a system, real time monitor is available locally (e.g., via the LAN) and is further available non-locally (e.g., via the WAN). Note that any of the user computing devices 14 may receive data from the any of the sensor computing devices 12 via a combination of LANs and the WAN.

Figure 2:
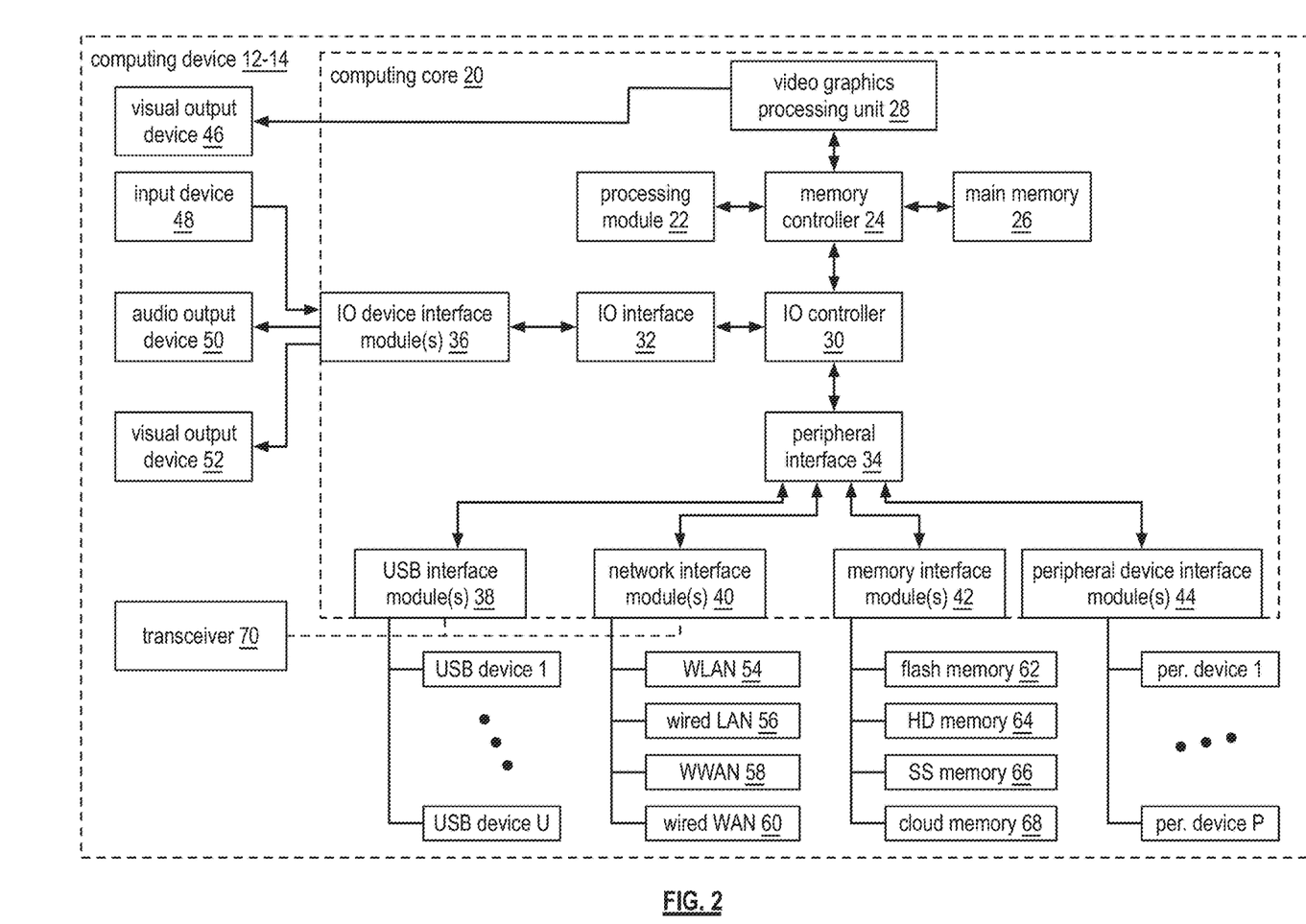
FIG. 2 is a schematic block diagram of an embodiment of a computing device in accordance with the present invention.

FIG. 2 is a schematic block diagram of an embodiment of a computing device 12 and/or 14 that includes a computing core 20, one or more input devices 48 (e.g., keypad, keyboard, touchscreen, voice to text, etc.), one or more audio output devices 50 (e.g., speaker(s), headphone jack, etc.), one or more visual output devices 46 (e.g., video graphics display, touchscreen, etc.), one or more universal serial bus (USB) devices, one or more networking devices (e.g., a wireless local area network (WLAN) device 54, a wired LAN device 56, a wireless wide area network (WWAN) device 58 (e.g., a cellular telephone transceiver, a wireless data network transceiver, etc.), and/or a wired WAN device 60), one or more memory devices (e.g., a flash memory device 62, one or more hard drives 64, one or more solid state (SS) memory devices 66, and/or cloud memory 96), one or more peripheral devices, and/or a transceiver 70.

The computing core 20 includes a video graphics processing unit 28, one or more processing modules 22, a memory controller 24, main memory 26 (e.g., RAM), one or more input/output (I/O) device interface module 36, an input/output (I/O) interface 32, an input/output (I/O) controller 30, a peripheral interface 34, one or more USB interface modules 38, one or more network interface modules 40, one or more memory interface modules 42, and/or one or more peripheral device interface modules 44. Each of the interface modules 36-44 includes a combination of hardware (e.g., connectors, wiring, etc.) and operational instructions stored on memory (e.g., driver software) that is executed by the processing module 22 and/or a processing circuit within the respective interface module. Each of the interface modules couples to one or more components of the computing device 12-14. For example, one of the IO device interface modules 36 couples to an audio output device 50.

As another example, one of the memory interface modules 42 couples to flash memory 62 and another one of the memory interface modules 42 couples to cloud memory 68 (e.g., an on-line storage system and/or on-line backup system).

The transceiver 70 is coupled to the computing core 20 via a USB interface module 38, a network interface module 40, a peripheral device interface module 44, or a dedicated interface module (not shown). Regardless of how the transceiver 70 is coupled to the computing core, it functions to communication with the passive wireless sensors.

Figure 3:
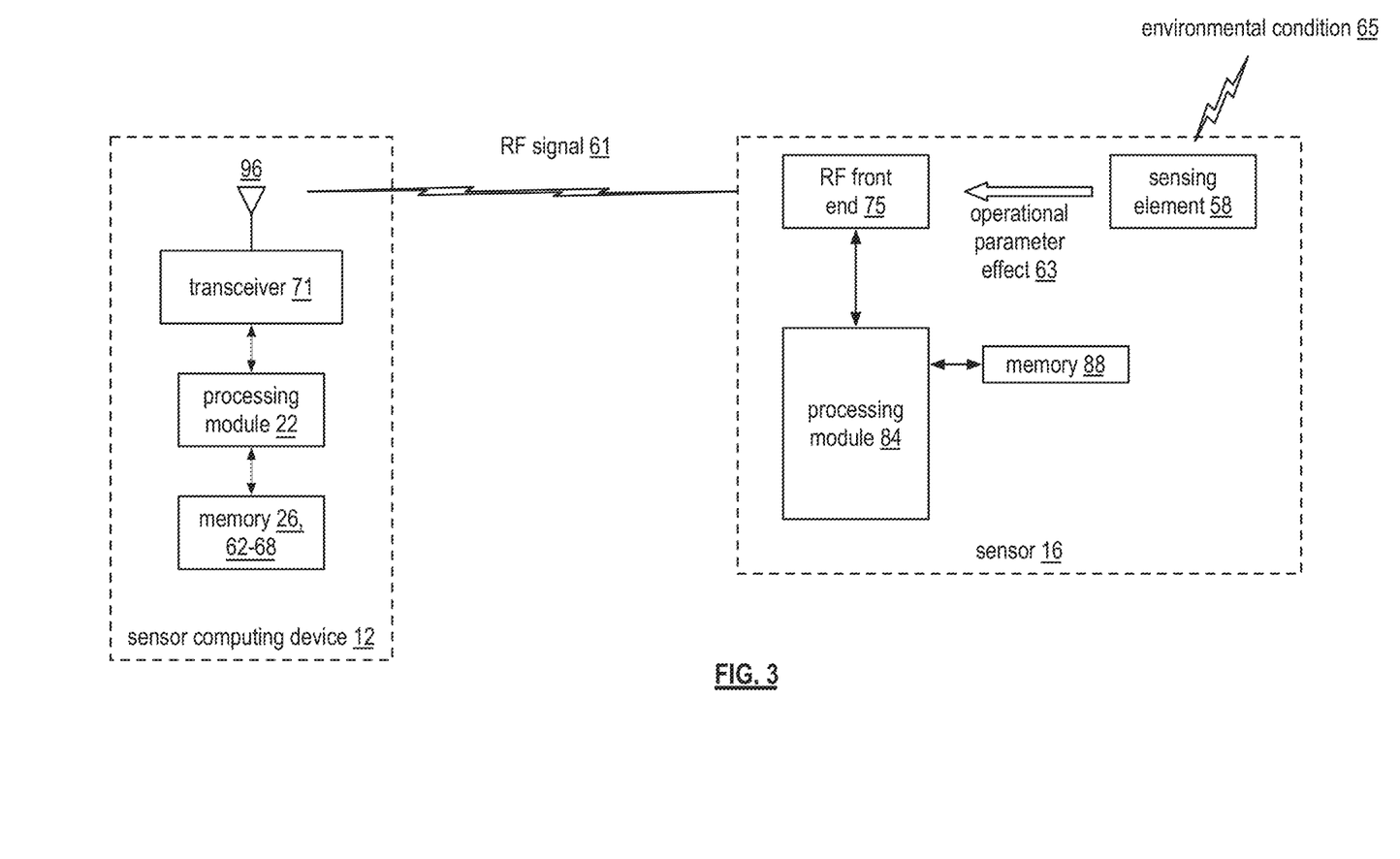
FIG. 3 is a schematic block diagram of an example of a sensor computing device communicating with a wireless sensor in accordance with the present invention.

FIG. 3 is a schematic block diagram of an example of a sensor computing device 12 communicating with a wireless sensor 16 (e.g., any one of 16-1 through 16-4). The sensor computing device 12 is illustrated in a simplified manner; as such, it shown to include the transceiver 71, an antenna 96, the processing module 22, and the memory (e.g., one or more 26 and 62-68). The wireless sensor 16 includes an RF front end 75 (e.g., receiver section, transmitter section, antenna, and/or a tuning circuit), a processing module 84, and memory 88.

In an example, the sensing element 58 of the wireless sensor 16 senses an environmental condition 65 of an object or item. The environment condition 65 includes, but is not limited to, one or more of moisture, temperature, pressure, humidity, altitude, sonic wave (e.g., sound), human contact, surface conditions, tracking, location, etc. The object or item includes one or more of, but is not limited to, a box, a personal item (e.g., clothes, diapers, etc.), a pet, an automobile component, an article of manufacture, an item in transit, blood, liquid, gas, etc. The sensing element 58 senses the environmental condition (e.g., moisture) and, as a result of the sensed condition, the sensing element 58 affects 63 an operational parameter (e.g., input impedance, quality factor, frequency, etc.) of an RF front end 75.

As a specific example, the sensing element 58, as a result of the sensed environmental condition 65, affects the input impedance of the antenna structure and/or of the tuning circuit (e.g., a tank circuit that includes one or more capacitors and one or inductors having a resonant frequency corresponding to the carrier frequency of the RF signal) of the RF front end 75. In response to the impedance change, the processing module 84 adjusts the resonant frequency of the tuning circuit to compensate for the change in input impedance caused by the sensed environmental condition. The amount of adjustment is reflective of the level of the environmental condition (e.g., a little change corresponds to a little moisture; a large change corresponds to a large amount of moisture). The processing module 84 generates a coded digital value to represent the amount of adjustment and conveys the coded value to the sensor computing device 12 via the transmitter section and the antenna of the RF front end 75 using back-scattering.

In addition to processing the sensed environmental condition, the processing module 84 processes a power level adjustment. For example, a power detection circuit of the wireless sensor 16 detects a power level of a received RF signal. In one embodiment, the processing module interprets the power level and communicates with the sensor computing device 12 to adjust the power level of the RF signal transmitted by the computing device 12 to a desired level (e.g., optimal for accuracy in detecting the environmental condition). In another embodiment, the processing module 84 includes the received power level data with the environmental sensed data it sends to the sensor computing device 12 so that the computing device can factor the power level into the determination of the environmental condition.

Figure 4:
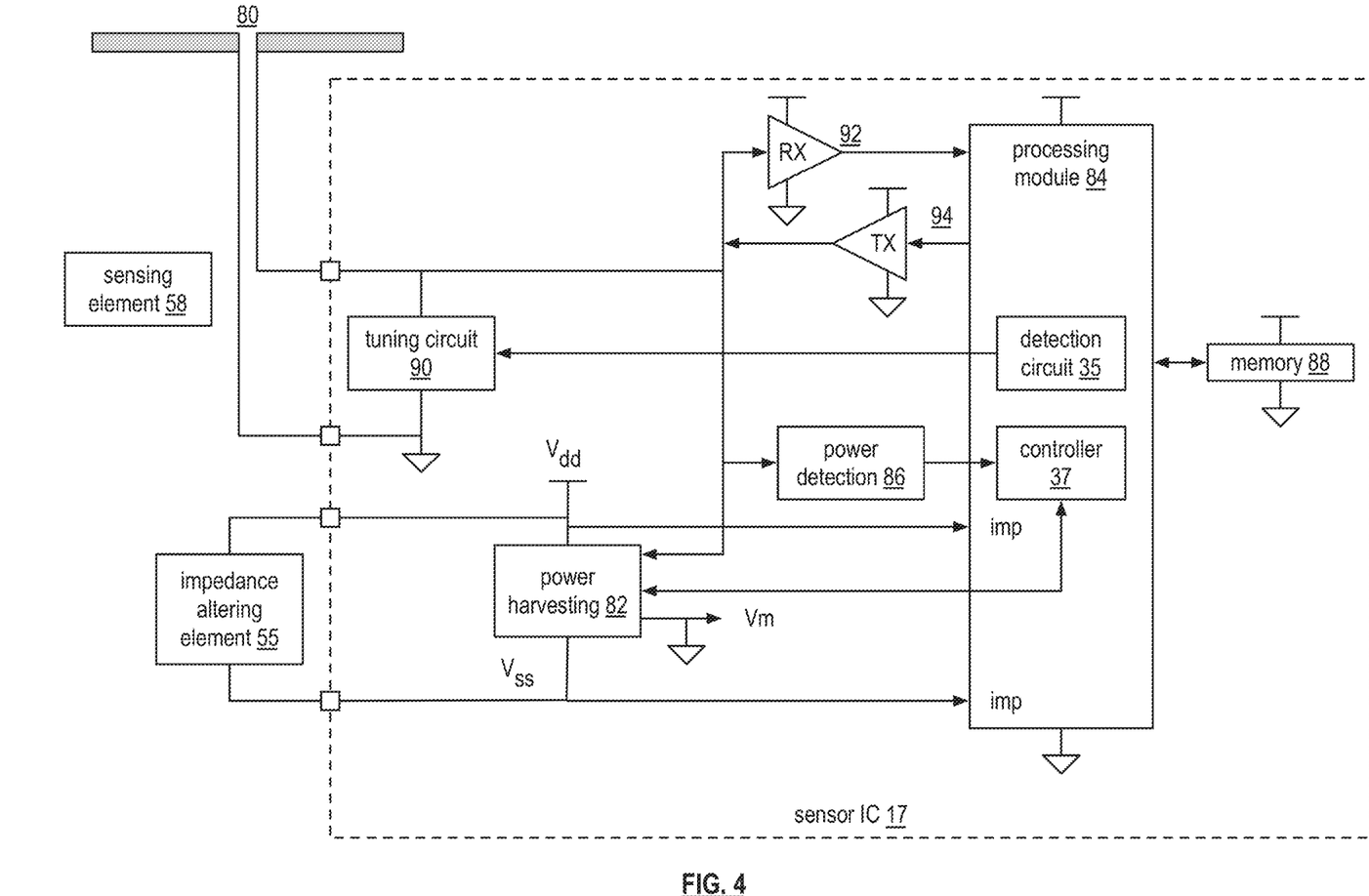
FIG. 4 is a schematic block diagram of an embodiment of a wireless sensor in accordance with the present invention.

FIG. 4 is a schematic block diagram of an embodiment of a wireless sensor that includes a substrate 100, an antenna 80 (e.g. dipole, monopole, spiral, meandering trace, etc.), a transmission line 102, the sensing element 58, a power supply impedance altering element 55, and a sensor integrated circuit (IC) 17. The sensor IC 17 includes the processing module 84, the memory 88, a transmitter section 94, a receiver section 92, a power harvesting circuit 82, a power detection circuit 86, and a tuning circuit 90. The processing module 84 is configured to include a controller 37 and a detection circuit 35.

In an example of operation, the wireless sensor is associated with an item and an identifier of the item is stored in the memory 88. The item is one or more of a gas, liquid, solid, composition, article or manufacture, a bodily fluid (e.g., urine, blood, saliva, etc.), an animal, and an inanimate object (e.g., a wall, a chair, an automobile part, etc.). The wireless sensor may be directing attached to the item or it may sense the item through the item's container (e.g., sensing temperature and/or level of blood in a bag).

In many instances, it is desirable to obtain multiple pieces of information about the condition of an item. For example, for a bag of blood it is desirable to measure both the temperature and level. As another example, for a diaper, it is desirable to measure both the amount of liquid and the electrolyte level of the liquid. As yet another example, for a steering wheel it is desirable to determine the rotational orientation of the steering wheel as well as the presence of one or more hands on it.

In other instances, it is desirable to obtain information about two different locations of an item using one wireless sensor. For example, in automotive testing for leaks, it is desirable to test two locations via one wireless sensor for leaks. As another example, for refrigerated products, it is desirable to measure the temperature at multiple locations for consistency of temperature. As yet another example, for dipping products in a liquid solution for cleaning, for processing, etc., it is desirable to measure fluid levels at multiple points on the product.

To accomplish this, the wireless sensor includes the sensing element 58 and the power supply impedance altering element 55. The sensing element 58 sensing a condition of an item and, based on the condition, changes an RF characteristic of the RF front end of the wireless sensor. The sensing element 58 may be one of a variety of sensors that senses one or more of a variety of conditions. For example, the sensing element measures the temperatures of fluids, such as blood bags. As another example, the sensing element senses moisture or temperature inside of a container. As yet another example, the sensing element senses moisture or temperature at a location with overlaying metal or electronics that block the RF signal (e.g., the floor of a car, a metallic panel, a speaker, an audio amplifier, other electronics, a crib, a mattress pad, etc.). As a further example, the sensing element senses moisture or temperature at location that is physically too small to fit an antenna but can accommodate the tip of the tail.

The power supply impedance altering element 55 senses another condition of the item and, based on the condition, changes the impedance of the power harvesting circuit 82. As an example, the power supply impedance altering element 55 is potentiometer that measures angular rotation of a shaft. As another example, the power supply impedance altering element 55 includes a first metallic trace coupled to the first power supply connection and a second metallic trace coupled to the second power supply connection, wherein the sensing element is operable to detect the presence or absence of moisture.

For the sensing computing device 12 to communicate with the wireless sensor 16, the sensor 16 first generates a power supply voltage (or multiple power supply voltages) from an RF (radio frequency) signal transmitted by the sensing computing device 12. For example, the RF signal 61 is a continuous wave signal and uses amplitude shift keying (ASK) or other amplitude-based modulation scheme to convey data.

The power harvesting circuit 82 receives the RF signal 61 via the antenna 80 and converts it into one or more supply voltages (Vs). The supply voltage(s) power the other components (e.g., 84, 86, 92 and 94) so that they perform their specific tasks. For instance, the receiver 92 is operable to convert an inbound message received from the sensing computing device into a baseband signal that it provides to the processing module 84. The processing module 84 processes the baseband signal and, when appropriate, generates a response that is subsequently transmitted via the antenna 80 by the transmitter 94. For example, the inbound message instructs the wireless sensor to provide a respond with a pressure, temperature, or moisture level measurement and the stored ID of the item.

To obtain a measurement of a condition of the item, the sensing circuit 58 senses the item. For instance, the sensing circuit 58 is producing a change to one or more of capacitance, inductance, resistance, resonant frequency, and antenna loading of the wireless sensor as an indication of the condition of the item. For example, when the sensing element 58 is sensing for moisture, as the presence of moisture increases, the impedance of the sensing element will decrease affecting one or more of the capacitance, inductance, resistance, and antenna loading of the wireless sensor. As another example, when the sensing element 58 is sensing for gases, its resistance changes in the presence of gases such as $CO$, $CO_2$, $NOx$, $H_2S$, $O_2$, and Cb. As a further example, when the sensing element is sensing for proximity, movement, or pressure, the sensing element experiences inductive changes created by eddy currents on nearby metal surfaces.

The changing electrical characteristics of the sensing circuit 58 causes a change in an RF characteristic of the RF front end 75, which includes the antenna 80, the tuning circuit 90, and the sensing circuit 58. Note that an RF characteristic includes an impedance (e.g., an input impedance) at a frequency (e.g., carrier frequency of the RF signal), a resonant frequency (e.g., of the turning circuit and/or antenna), a quality factor (e.g., of the antenna), and/or a gain. As a specific example, the resonant frequency has changed from a desired resonant frequency (e.g., matching the carrier frequency of the RF signal) as result of the sensed condition.

The processing module 84 detects, via the detection circuit 35, a variance of the one or more RF characteristics from a desired value (e.g., the resonant frequency changes from a desired frequency that corresponds to the carrier frequency of the RF signal). When the processing module detects the variance, it adjusts the tuning circuit to substantially re-establish the desired value of the one or more RF characteristics. For example, the tuning circuit 90 includes an inductor and a capacitor, at least one of which is adjusted to change the resonant frequency back to the desired value.

The processing module 84 determines the amount of adjusting of the tuning circuit 90 and converts the amount of adjusting into a digital value. The digital value is representative of the sensed condition of the item by the sensing circuit 58. For example, the digital value represents a change in the condition with respect to a reference condition (increasing temperature, increasing moisture level, etc.). As another example, the digital represents a measure of the condition (e.g., a temperature, a moisture level, a pressure level, etc.).

The processing module 84 generates a message regarding the adjusting of the tuning circuit (e.g., the message includes the digital value or an actual measurement if the processing module performs a digital value to measurement conversion function). The transmitter 94 transmits the message to the sensing computing device 12 via the antenna 80 or another antenna (not shown).

To obtain a measurement of the other condition of the item, the power supply impedance altering element 55 senses the item. Based on the condition, the power supply impedance altering element 55 changes the impedance of the power harvesting circuit 82. For example, when the power supply impedance altering element 55 is sensing for moisture, as the presence of moisture increases, the impedance of the sensing element will decrease affecting the impedance of the power harvesting circuit. As another example, an impedance change on power supply connections effects the detection circuit that results in a detectable change in the sensor codes that can be measured and read.

The processing module 84 detects an impedance change of the power supply based on an effect of the power supply impedance altering element 55. The processing module 84 then converts the impedance change into a digital value that is representative of the condition of the item. The wireless sensor then outputs, via the antenna, the digital value or a representation of the condition of the item. As a specific example, the detection circuit adjusts the input capacitance to peak up the voltage using a peak voltage detector. The process results in a close approximation to a conjugate impedance match for resonant, low-loss circuits. For higher loss circuits, the peak voltage occurs for capacitance values that are lower than that required for conjugate match. In addition, the sensor codes are pulled lower as losses increase. Such a pulling of the sensor codes with losses enables the power harvesting circuit 82 to be used as a sensor. Increasing the current drawn through a power harvesting circuit increases the power dissipation of the sensor IC as a whole and this, in turn, causes an increase in the input resistance. Basically, a change in conductivity at the voltage supply terminals. The higher the input resistance is, the lower the sensor codes will register.

Before the processing module 84 processes one or both of the sensed conditions, it may perform a power level adjustment. For example, the power detection circuit 86 detects a power level of the received RF signal. In one embodiment, the processing module interprets the power level and communicates with the sensing computing device 12 to adjust the power level of the RF signal to a desired level (e.g., optimal for accuracy in detecting the environmental condition). In another embodiment, the processing module includes the received power level data with the digital it sends to the sensing computing device 12 so that the computing device 12 can factor the power level into the determination of the extent of the condition.

The processing module 84 may be further operable to perform a calibration function when the condition in which the sensor is known (e.g., in a room at a certain altitude, in a calibration chamber having a set pressure, at a known temperature, etc.). For example, the processing module 84 receives a calibration request from a sensing computing device. In response, the processing module adjusts the tuning circuit to establish the desired value of the RF characteristic(s) (e.g., resonant frequency, input impedance, quality factor, gain, etc.). The processing module then records a level of the adjusting of the tuning circuit to represent a calibration digital value of the wireless sensor (e.g., records a digital value). The processing module may communicate the calibration value to the sensing computing device 12 as part of the calibration process or send it along with the digital value of a condition measurement.

Figure 5:
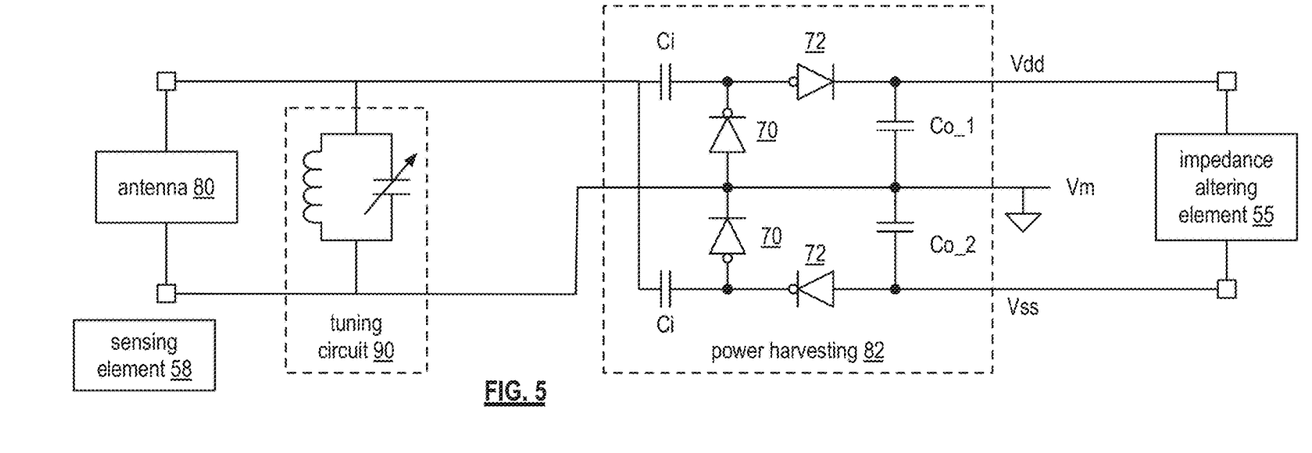
FIG. 5 is a schematic block diagram of an embodiment of a tuning circuit and power harvesting circuit of a wireless sensor in accordance with the present invention.

FIG. 5 is a schematic block diagram of an embodiment of a tuning circuit 90 and power harvesting circuit 82 of a wireless sensor 16 coupled to the power supply impedance altering element 55. The tuning circuit 90 includes an inductor and an adjustable capacitor (e.g., a varactor, a switchable capacitor bank, etc.). As the impedance altering element 55 decreases the impedance of the power harvesting circuit, the tuning circuit 90 is adjusted as described above to compensate for the decreasing power harvesting circuit impedance. The amount of adjust corresponds to the condition of the item being sensed.

The power harvesting circuit 82 includes two n-channel circuits 70, two p-channel circuits 72, two capacitance circuits (Ci), and two output capacitance circuits (Co). In this configuration, the power harvesting circuit 82 creates two voltages: The first voltage is created by the upper half of the power harvesting circuit across Co_1 and the second voltage is created by the lower half of the power harvesting circuit across Co_2. A further discussion of this power harvesting circuit is provided in co-pending patent application having a U.S. Utility application Ser. No. 13/732,263, entitled "AC-TO-DC CHARGE PUMP HAVING A CHARGE PUMP AND COMPLIMENTARY CHARGE PUMP", and filed on Dec. 31, 2012.

Figure 6:
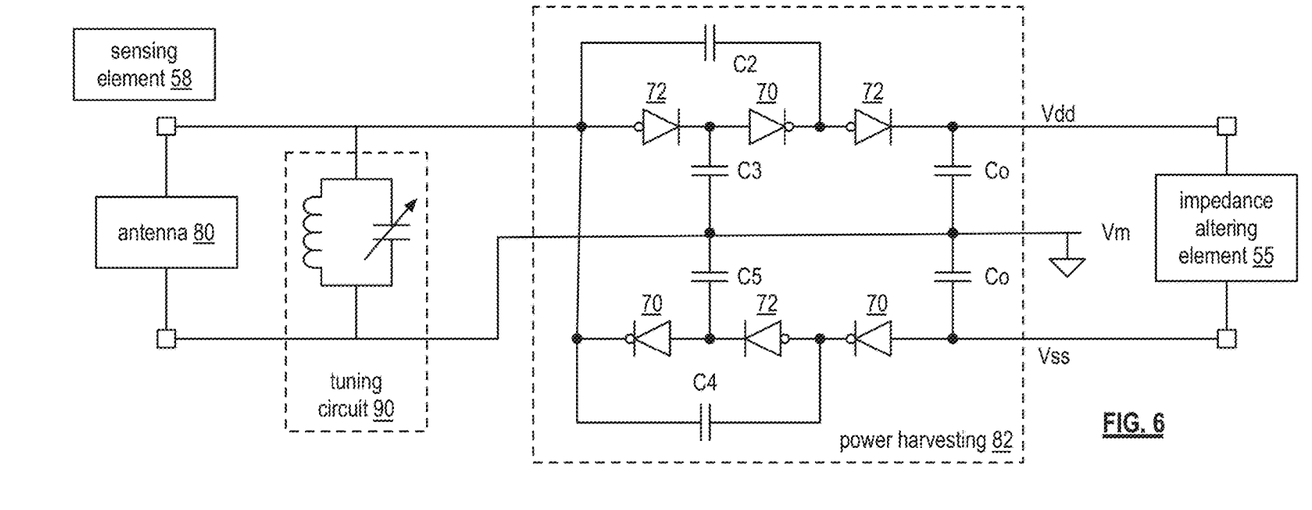
FIG. 6 is a schematic block diagram of another embodiment of a tuning circuit and power harvesting circuit of a wireless sensor in accordance with the present invention.

FIG. 6 is a schematic block diagram of another embodiment of a tuning circuit 90 and power harvesting circuit 82 of a wireless sensor 16 coupled to the power supply impedance altering element 55. This embodiment functions similarly to the embodiment of FIG. 5 with the difference being the implementation of the power harvesting circuit 82. In this embodiment, the power harvesting circuit 82 includes a three diode three capacitor upper half and a three diode three capacitor lower half.

The three diode three capacitor upper half includes an n-channel circuit 70, two p-channel circuits 72, a first capacitance circuit (C2), a second capacitance circuit (C3) and a third capacitance circuit (Co). Each of the capacitance circuits includes one or more of: one or more capacitors, one or more varactors, and/or one or more transistors configured to function as a capacitor. Each of the p-channel circuits include a first diode element, a first diode voltage reduction circuit coupled to reduce a diode voltage of the first diode element, and a first start-up current circuit operably coupled to increase start-up current of the first diode element as previously discussed. The n-channel circuit includes a second diode element, a second diode voltage reduction circuit coupled to reduce a diode voltage of the second diode element, and a second start-up current circuit operably coupled to increase start-up current of the second diode element as previously discussed.

As shown, the first capacitance circuit (C2) is coupled to a first leg of a received radio frequency (RF) signal and to the first p-channel circuit. The first p-channel circuit is further coupled to the second capacitor circuit (C3) and to the n-channel circuit. The n-channel circuit is further coupled to the first capacitance circuit (C2) and to the second p-channel circuit. The second p-channel circuit is further coupled to the third capacitance circuit (Co) to provide an output voltage and the second and third capacitance circuits are further coupled to a second leg of the RF signal. The power harvesting circuit is further discussed in the co-pending patent application having a U.S. Utility application Ser. No. 13/732,263, entitled "AC-TO-DC CHARGE PUMP HAVING A CHARGE PUMP AND COMPLIMENTARY CHARGE PUMP", and filed on Dec. 31, 2012.

Figure 7:
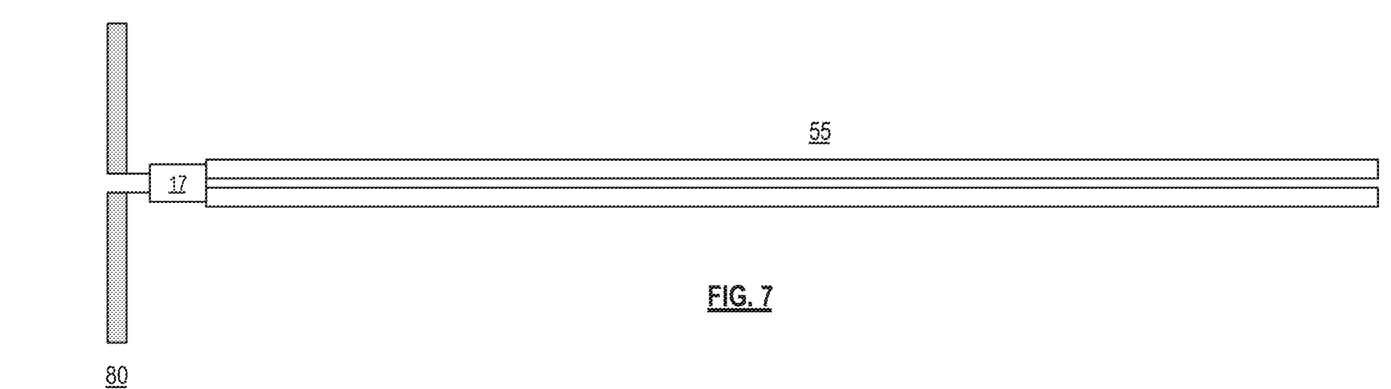
FIG. 7 is a schematic block diagram of another embodiment of a wireless sensor in accordance with the present invention.

FIG. 7 is a schematic block diagram of another embodiment of a wireless sensor 16 that includes the antenna 80, the sensor IC 17, and the power supply impedance altering element 55. In this embodiment, the power supply impedance altering element includes a sensing element having a first metallic trace coupled to the first power supply connection and a second metallic trace coupled to the second power supply connection. In this configuration, the sensing element is operable to detect the presence or absence of moisture.

In an example of operation, the sensor IC 17 draws about 5 micro-amps of current at minimum operational power levels. When moisture is present on the metallic traces (e.g., comprised of any electrically conductive metal or other electrically conductive material), current is pulled through the traces. To significantly pull the sensor codes, the current draw needs to make a significant change, which can be accomplished by doubling the current draw. As such, when the ends of the metallic traces are immersed in fluid (e.g., water), then the impedance of the power supply impedance altering element 55 should be above 200 Kilo-Ohms so that is draws 5 micro-amps at 1 volt.

Figure 8:
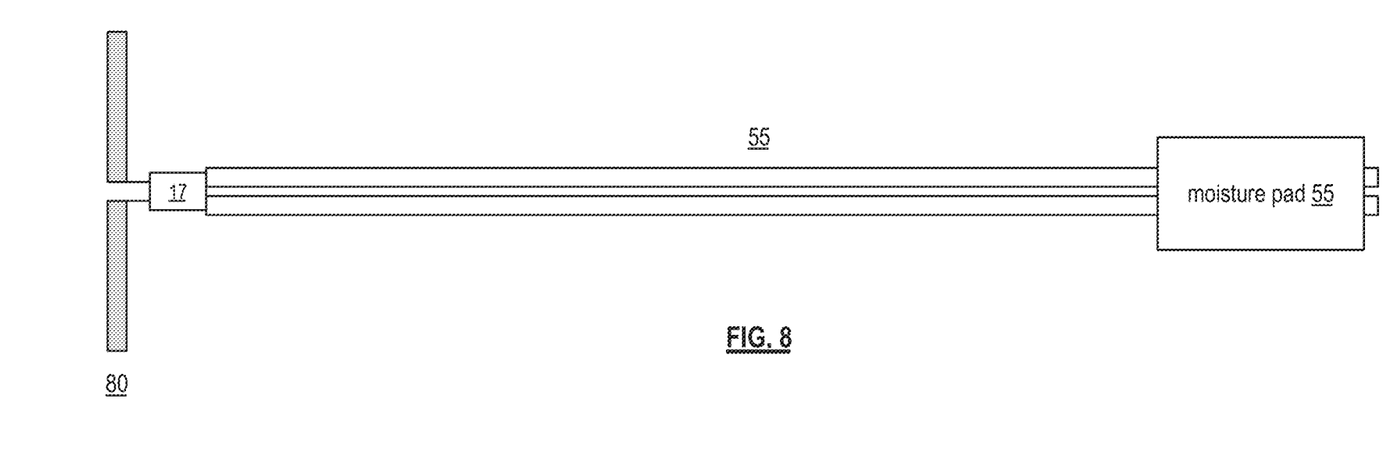
FIG. 8 is a schematic block diagram of another embodiment of a wireless sensor in accordance with the present invention.

FIG. 8 is a schematic block diagram of another embodiment of a wireless sensor 16 that includes the antenna 80, the sensor IC 17, the power supply impedance altering element 55, and a moisture pad 57. This embodiment is similar to the embodiment of FIG. 8 with the inclusion of the moisture pad 57 positioned at the end of the two metallic traces. The moisture pad 57 functions to capture moisture and/or an electrolyte content of a fluid.

As a specific example, the moisture pad 57 is paper to hold the water in place. Each of the traces is 0.5 oz copper with gold flash on 5 mil Kapton and a 90 µm air gap between them. With no electrolyte, the DC resistance of the power supply impedance altering element 55 is around 2 M Ohm. This is equivalent to a DC open and is high enough that it would not result in any significant movement of the sensor code. Immersing the moisture pad 57 in water fully saturated by salt results in a DC resistance of about 300 k Ohms. The change in minimum power would be related to the change in power consumption: Dry: P1=1 V*5 µA=5 µW; Wet: P=1 V*(5 µA+1 V/300 kQ)=8.3 µW. The change in sensitivity is therefore approximately 10*log 10(8.3/5)=2.2 dB. Note that RF chokes or ferrite beads may be used to reduce any adverse RF effects that may be causes the metallic traces.

Figure 9:
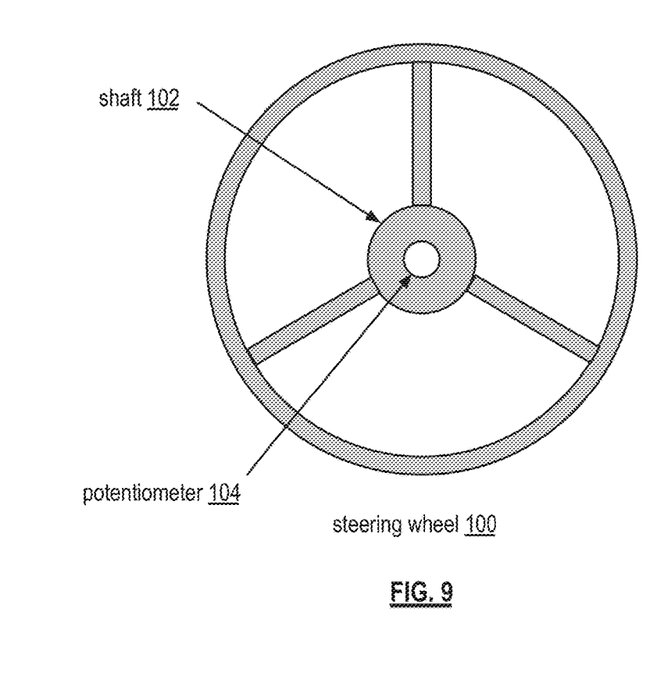
FIG. 9 is a schematic block diagram of an embodiment of a sensing element on a steering wheel in accordance with the present invention.

FIG. 9 is a schematic block diagram of an embodiment of a sensing element on a steering wheel 100. The steering wheel 100 includes a shaft about which the wheel rotates. A potentiometer 104 is attached to the shaft 102. The impedance of the potentiometer changes as the shaft is rotated. This impedance change effects the impedance of the power harvesting circuit 82, which can be measured as discussed above. As such, by measuring the impedance change, the angular rotation of the shaft 102 can be measured.

Figures 10, 11:
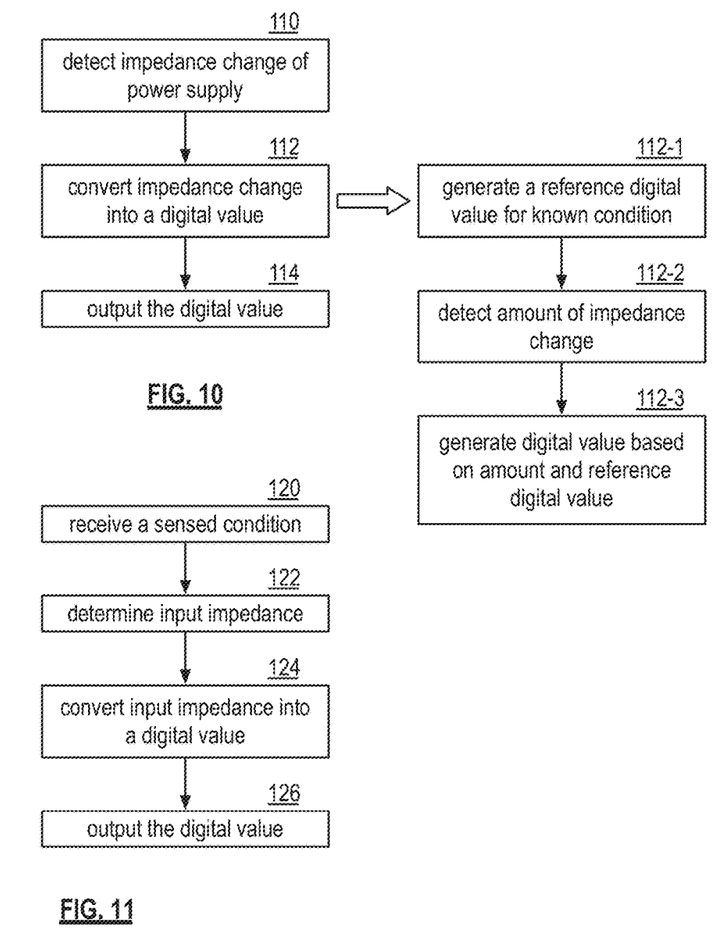
FIG. 10 is a logic diagram of an embodiment of a method for a wireless sensor to generate a digital value in accordance with the present invention.
FIG. 11 is a logic diagram of another embodiment of a method for a wireless sensor to generate a digital value in accordance with the present invention.

FIG. 10 is a logic diagram of an embodiment of a method for a wireless sensor to generate a digital value begins at step 110 where the sensor IC detects an impedance change of the power supply based on an effect of the power supply impedance altering element. The effect may be the result of a change in water vapor detection, sensing of wet material stock when wetness causes product loss or deterioration, sensing of wetness in applications sensitive to mold or corrosion (e.g. in drywall), detecting leaks in hard-to-access locations and diapers for adults and children.

The method continues at step 112 where the sensor IC converts the impedance change into a digital value that is representative of the condition of the item. For instance, the sensor IC generates, at step 112-1, a reference digital value for a known impedance of the power supply that corresponds to a known condition of the item (e.g., known dry condition). The sensor IC then detects, at step 112-2, an amount of the impedance change of the power supply based on the effect of the power supply impedance altering element. The sensor IC then generates, at step 112-3, the digital value based on the amount of impedance change and the known impedance of the power supply for the known condition of the item. The method continues at step 114 where the sensor IC outputs, via the antenna, the digital value or a representation of the condition of the item.

FIG. 11 is a logic diagram of another embodiment of a method for a wireless sensor that begins at step 120 where the sensor IC of the wireless sensor receives a sensed condition of the item from the sensing element 58 (e.g., a change in an RF characteristic of the RF front end). The method continues at step 122 where the sensor IC determines an input impedance of the wireless sensor based on the sensed condition. For example, the sensor IC determines a change in the resonant frequency of the RF front end, which corresponds to a change in the input impedance of the RF front end of the wireless sensor.

The method continues at step 124 where the sensor IC converts the input impedance into a digital value that is representative of the condition of the item. For example, the sensor IC adjusts the tuning circuit such that the resonant frequency of the RF front end substantially matches the frequency of the received RF signal. The adjustment amount of the tuning circuit is determined and converted into the digital value. The method continues at step 126 where the sensor IC outputs, via the antenna, the digital value or a representation of the condition of the item (e.g., the sensor IC interprets the digital value to determine a measure of the condition of the item). Note that the condition of the second item includes a change in the condition with respect to a reference condition and/or a measure of the second condition. Further note that the second condition includes temperature; moisture; pressure; concentration level of the item; and/or presence or absence detection of the item.

It is noted that terminologies as may be used herein such as bit stream, stream, signal sequence, etc. (or their equivalents) have been used interchangeably to describe digital information whose content corresponds to any of a number of desired types (e.g., data, video, speech, audio, etc. any of which may generally be referred to as 'data').

As may be used herein, the terms "substantially" and "approximately" provides an industry-accepted tolerance for its corresponding term and/or relativity between items. Such an industry-accepted tolerance ranges from less than one percent to fifty percent and corresponds to, but is not limited to, component values, integrated circuit process variations, temperature variations, rise and fall times, and/or thermal noise. Such relativity between items ranges from a difference of a few percent to magnitude differences. As may also be used herein, the term(s) "configured to", "operably coupled to", "coupled to", and/or "coupling" includes direct coupling between items and/or indirect coupling between items via an intervening item (e.g., an item includes, but is not limited to, a component, an element, a circuit, and/or a module) where, for an example of indirect coupling, the intervening item does not modify the information of a signal but may adjust its current level, voltage level, and/or power level. As may further be used herein, inferred coupling (i.e., where one element is coupled to another element by inference) includes direct and indirect coupling between two items in the same manner as "coupled to". As may even further be used herein, the term "configured to", "operable to", "coupled to", or "operably coupled to" indicates that an item includes one or more of power connections, input(s), output(s), etc., to perform, when activated, one or more its corresponding functions and may further include inferred coupling to one or more other items. As may still further be used herein, the term "associated with", includes direct and/or indirect coupling of separate items and/or one item being embedded within another item.

As may be used herein, the term "compares favorably", indicates that a comparison between two or more items, signals, etc., provides a desired relationship. For example, when the desired relationship is that signal 1 has a greater magnitude than signal 2, a favorable comparison may be achieved when the magnitude of signal 1 is greater than that of signal 2 or when the magnitude of signal 2 is less than that of signal 1. As may be used herein, the term "compares unfavorably", indicates that a comparison between two or more items, signals, etc., fails to provide the desired relationship.

As may also be used herein, the terms "processing module", "processing circuit", "processor", and/or "processing unit" may be a single processing device or a plurality of processing devices. Such a processing device may be a microprocessor, micro-controller, digital signal processor, microcomputer, central processing unit, field programmable gate array, programmable logic device, state machine, logic circuitry, analog circuitry, digital circuitry, and/or any device that manipulates signals (analog and/or digital) based on hard coding of the circuitry and/or operational instructions. The processing module, module, processing circuit, and/or processing unit may be, or further include, memory and/or an integrated memory element, which may be a single memory device, a plurality of memory devices, and/or embedded circuitry of another processing module, module, processing circuit, and/or processing unit. Such a memory device may be a read-only memory, random access memory, volatile memory, non-volatile memory, static memory, dynamic memory, flash memory, cache memory, and/or any device that stores digital information. Note that if the processing module, module, processing circuit, and/or processing unit includes more than one processing device, the processing devices may be centrally located (e.g., directly coupled together via a wired and/or wireless bus structure) or may be distributedly located (e.g., cloud computing via indirect coupling via a local area network and/or a wide area network). Further note that if the processing module, module, processing circuit, and/or processing unit implements one or more of its functions via a state machine, analog circuitry, digital circuitry, and/or logic circuitry, the memory and/or memory element storing the corresponding operational instructions may be embedded within, or external to, the circuitry comprising the state machine, analog circuitry, digital circuitry, and/or logic circuitry. Still further note that, the memory element may store, and the processing module, module, processing circuit, and/or processing unit executes, hard coded and/or operational instructions corresponding to at least some of the steps and/or functions illustrated in one or more of the Figures. Such a memory device or memory element can be included in an article of manufacture.

One or more embodiments have been described above with the aid of method steps illustrating the performance of specified functions and relationships thereof. The boundaries and sequence of these functional building blocks and method steps have been arbitrarily defined herein for convenience of description. Alternate boundaries and sequences can be defined so long as the specified functions and relationships are appropriately performed. Any such alternate boundaries or sequences are thus within the scope and spirit of the claims. Further, the boundaries of these functional building blocks have been arbitrarily defined for convenience of description. Alternate boundaries could be defined as long as the certain significant functions are appropriately performed. Similarly, flow diagram blocks may also have been arbitrarily defined herein to illustrate certain significant functionality.

To the extent used, the flow diagram block boundaries and sequence could have been defined otherwise and still perform the certain significant functionality. Such alternate definitions of both functional building blocks and flow diagram blocks and sequences are thus within the scope and spirit of the claims. One of average skill in the art will also recognize that the functional building blocks, and other illustrative blocks, modules and components herein, can be implemented as illustrated or by discrete components, application specific integrated circuits, processors executing appropriate software and the like or any combination thereof.

In addition, a flow diagram may include a "start" and/or "continue" indication. The "start" and "continue" indications reflect that the steps presented can optionally be incorporated in or otherwise used in conjunction with other routines. In this context, "start" indicates the beginning of the first step presented and may be preceded by other activities not specifically shown. Further, the "continue" indication reflects that the steps presented may be performed multiple times and/or may be succeeded by other activities not specifically shown. Further, while a flow diagram indicates a particular ordering of steps, other orderings are likewise possible provided that the principles of causality are maintained.

The one or more embodiments are used herein to illustrate one or more aspects, one or more features, one or more concepts, and/or one or more examples. A physical embodiment of an apparatus, an article of manufacture, a machine, and/or of a process may include one or more of the aspects, features, concepts, examples, etc. described with reference to one or more of the embodiments discussed herein. Further, from figure to figure, the embodiments may incorporate the same or similarly named functions, steps, modules, etc. that may use the same or different reference numbers and, as such, the functions, steps, modules, etc. may be the same or similar functions, steps, modules, etc. or different ones.

While the transistors in the above described figure(s) is/are shown as field effect transistors (FETs), as one of ordinary skill in the art will appreciate, the transistors may be implemented using any type of transistor structure including, but not limited to, bipolar, metal oxide semiconductor field effect transistors (MOSFET), N-well transistors, P-well transistors, enhancement mode, depletion mode, and zero voltage threshold (VT) transistors.

Unless specifically stated to the contra, signals to, from, and/or between elements in a figure of any of the figures presented herein may be analog or digital, continuous time or discrete time, and single-ended or differential. For instance, if a signal path is shown as a single-ended path, it also represents a differential signal path. Similarly, if a signal path is shown as a differential path, it also represents a single-ended signal path. While one or more particular architectures are described herein, other architectures can likewise be implemented that use one or more data buses not expressly shown, direct connectivity between elements, and/or indirect coupling between other elements as recognized by one of average skill in the art.

The term "module" is used in the description of one or more of the embodiments. A module implements one or more functions via a device such as a processor or other processing device or other hardware that may include or operate in association with a memory that stores operational instructions. A module may operate independently and/or in conjunction with software and/or firmware. As also used herein, a module may contain one or more sub-modules, each of which may be one or more modules.

While particular combinations of various functions and features of the one or more embodiments have been expressly described herein, other combinations of these features and functions are likewise possible. The present disclosure is not limited by the particular examples disclosed herein and expressly incorporates these other combinations.

What is claimed is:

1. A wireless sensor comprises:
    a radio frequency (RF) front end that includes:
        an antenna for transceiving data via an RF signal; and
        a tuning circuit, wherein the tuning circuit adjust a resonant frequency of the RF front end to be approximately equal to a resonant frequency of the RF signal;
    a sensing integrated circuit (IC) that includes a power supply, a first power supply connection, and a second power supply connection, wherein the power supply generates a voltage from the RF signal; and
    a power supply impedance altering element coupled to the first and second power supply connections, wherein the power supply impedance altering element detects a condition of an item, wherein the sensing IC is operable to:
        detect an impedance change of the power supply based on an effect of the power supply impedance altering element;
        convert the impedance change into a digital value that is representative of the condition of the item; and
        output, via the antenna, the digital value or a representation of the condition of the item.

2. The wireless sensor of claim 1, wherein the power supply impedance altering element comprises:
    a sensing element that includes a first metallic trace coupled to the first power supply connection and a second metallic trace coupled to the second power supply connection, wherein the sensing element is operable to detect the presence or absence of moisture.

3. The wireless sensor of claim 2, wherein the sensing element further comprises:
    the first and second metallic traces are approximately parallel to each other and have a length, wherein a first end of the first metallic trace is coupled to the first power supply connection and a first end of the second metallic trace is coupled to the second power supply connection; and
    a moisture pad mounted at a second end of the first and second metallic traces for capturing at least one of moisture and an electrolyte content of a fluid.

4. The wireless sensor of claim 1, wherein the power supply impedance altering element comprises:
a potentiometer, wherein the item is a shaft of a rotating part, wherein, as the shaft is rotated, the potentiometer changes impedance of the power supply.

5. The wireless sensor of claim 1, wherein the sensing IC is further operable to:
generate a reference digital value for a known impedance of the power supply that corresponds to a known condition of the item;
detect an amount of the impedance change of the power supply based on the effect of the power supply impedance altering element; and
generate the digital value based on the amount of impedance change and the known impedance of the power supply for the known condition of the item.

6. The wireless sensor of claim 1 further comprises:
a sensing element for sensing a second condition of a second item, wherein, as the second condition changes, the sensing element changes an input impedance of the wireless sensor, wherein the sensing IC is operable to:
receive a sensed condition of the second item from the sensing element;
determine the input impedance of the wireless sensor based on the sensed condition;
convert the input impedance into a second digital value that is representative of the second condition of the second item; and
output, via the antenna, the second digital value or a representation of the second condition of the second item.

7. The wireless sensor of claim 6, wherein the second condition of the second item comprises one or more:
a change in the second condition with respect to a reference condition; and
a measure of the second condition.

8. The wireless sensor of claim 6, wherein the second condition of the item comprises one or more of:
temperature;
moisture;
pressure;
concentration level of the item; and
presence or absence detection of the item.

* * * * *